(12) United States Patent
Kuribayashi et al.

(10) Patent No.: US 7,060,092 B2
(45) Date of Patent: Jun. 13, 2006

(54) DEPLOYABLE STENT

(75) Inventors: Kaori Kuribayashi, Oxford (GB); Zhong You, Oxford (GB)

(73) Assignee: ISIS Innovation Limited, Oxford (GB)

( * ) Notice: Subject to any disclaimer, the term of this patent is extended or adjusted under 35 U.S.C. 154(b) by 221 days.

(21) Appl. No.: 10/473,232

(22) PCT Filed: Mar. 27, 2002

(86) PCT No.: PCT/GB02/01424

§ 371 (c)(1),
(2), (4) Date: Dec. 16, 2003

(87) PCT Pub. No.: WO02/078572

PCT Pub. Date: Oct. 10, 2002

(65) Prior Publication Data

US 2004/0098101 A1  May 20, 2004

(30) Foreign Application Priority Data

Mar. 29, 2001 (GB) .................................. 0107910.2

(51) Int. Cl.
*A61F 2/06* (2006.01)
(52) U.S. Cl. .................... 623/1.29; 623/1.28; 623/1.13
(58) Field of Classification Search .............. 623/1.11, 623/1.12, 1.15, 1.23, 1.28, 1.29, 1.35
See application file for complete search history.

(56) References Cited

U.S. PATENT DOCUMENTS

| 5,507,770 A | 4/1996 | Turk |
| 5,653,745 A | 8/1997 | Trescony et al. |
| 5,735,871 A | 4/1998 | Sgro |
| 5,800,515 A | 9/1998 | Nadal et al. |
| 5,855,597 A | 1/1999 | Jayaraman |
| 5,980,565 A * | 11/1999 | Jayaraman ................. 623/1.12 |
| 6,015,429 A * | 1/2000 | Lau et al. ..................... 623/1.2 |
| 6,053,938 A * | 4/2000 | Goldmann et al. ........ 623/1.15 |
| 6,106,549 A * | 8/2000 | Taheri ........................ 623/1.23 |
| 2002/0007222 A1* | 1/2002 | Desai ...................... 623/23.65 |
| 2002/0058984 A1* | 5/2002 | Butaric et al. ............. 623/1.13 |
| 2002/0068967 A1* | 6/2002 | Drasler et al. ............. 623/1.13 |
| 2003/0093142 A1* | 5/2003 | Edelman et al. .......... 623/1.15 |

FOREIGN PATENT DOCUMENTS

WO    WO 95/13033    5/1995

OTHER PUBLICATIONS

Serruys et al, "A Comparison of Balloon-Expandable-Stent Implantation with Balloon . . . ", N. Engl. J. Med. vol. 331(8), pp. 489-495, 1994.

(Continued)

*Primary Examiner*—Corrine McDermott
*Assistant Examiner*—Thomas J. Sweet
(74) *Attorney, Agent, or Firm*—Nixon & Vanderhye P.C.

(57) ABSTRACT

A stent 1 comprising a sheet 2 of biocompatible material arranged as a tube and having a pattern of folds allowing the stent to be collapsed for deployment. The pattern of folds comprises a unit cell repeated over the sheet 2. A variety of different unit cells 3 are described. The pattern of folds may progress helically around the tube which assists in implantation by synchronising deployment. The stent 1 prevents restenosis because it is formed of a continuous sheet 2, and allows slippage to be minimised.

31 Claims, 12 Drawing Sheets

OTHER PUBLICATIONS

Guitron, "Self-Expanding Metal Prosthesis as Palliative Treatment in Esophageal Cancer", Rev. Gastroenterol. Max., vol. 63(4), pp. 198-203, 1998.

Edelman et al, "Hoop Dreams Stents Without Restenosis", Circulation, vol. 94(6), pp. 1199-1202, 1996.

Hills et al, "Self-Expanding Metal Oesophageal Endoprostheses, Covered and Uncovered; A Review of 30 Cases", Eur. J. Gastroenterol Hepatol, vol. 10(5), pp. 371-374, 1998.

Adam et al, "A New Design of the Esophageal Wallstent Endoprosthesis Resistant to Distal Migration", AJR Am. J. Roentgenol., vol. 170(6), pp. 1477-1481, 1998.

Rogers et al, "Balloon-artery interactions during stent placement: a finite element analysis approach . . . ", Circ. Res. vol. 84(4), pp. 378-383, 1999.

Garasic et al, "Stent and Artery Geometry Determine Intimal Thickening Independent of Arterial Injury", Circulation, vol. 22, 101(7), pp. 812-818, 2000.

Kresling, "Self-Deployable Tubular Systems in Nature and Engineering", Structural Morphology Towards the New Millennium, 1997, pp. 188-195.

Kresling, "Coupled Mechanisms in Biological Deployable Structures", IHTAM-IASS Symposium on Deployable Structures: Theory and Applications, Sep. 6-9, 1998.

* cited by examiner $\alpha = 45°$
Pattern 1

$1° \leq \alpha < 45°$
Pattern 2

$45° < \alpha \leq 60°$
Pattern 3

Pattern 1-1

Pattern 2-1

Pattern 1-2

Pattern 2-2

Pattern 3-1

Pattern 1-3

Pattern 2-3

Pattern 4-1

Pattern 4-2

Pattern 4-3

Pattern 4-4

Pattern 5-1

Pattern 5-2

Pattern 5-3

Pattern 5-4

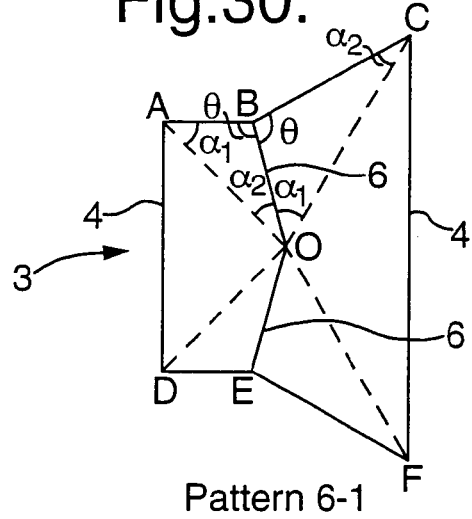
Fig.30. Pattern 6-1
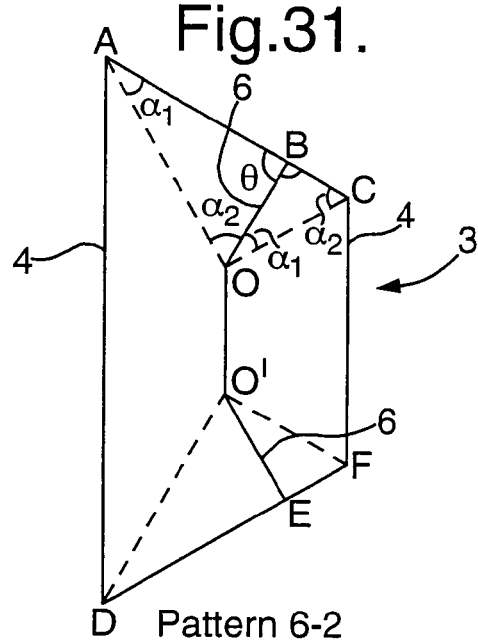
Fig.31. Pattern 6-2
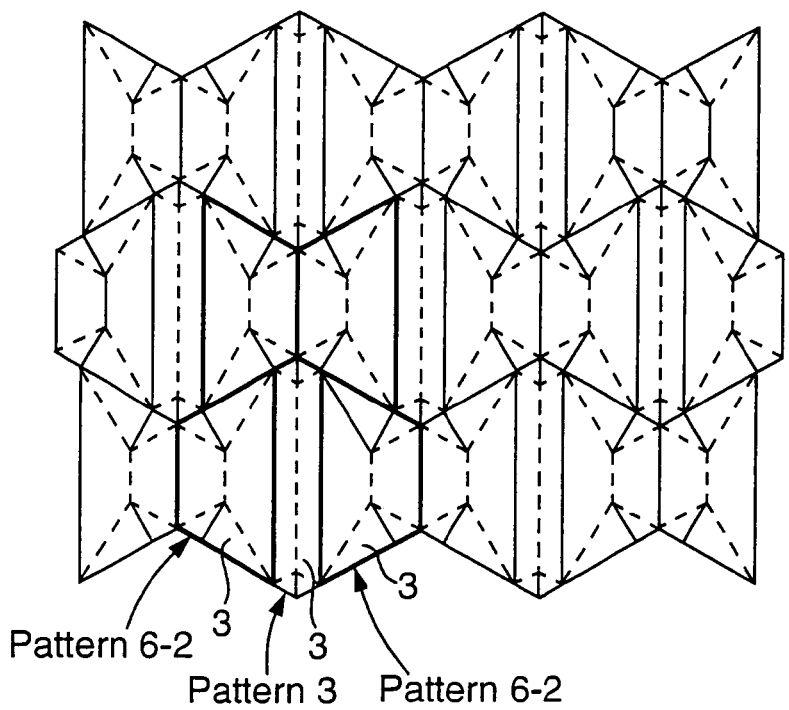
Fig.32.

Pattern 7-1

Pattern 7-2

DEPLOYABLE STENT

This application is the U.S. national phase of international application PCT/GB02/01424, filed Mar. 27, 2002, which designated the U.S.

The present invention relates to a stent. The present provides a novel structure for a stent, and also relates to the manufacture and use of the stent.

A stent is a medical device designed to open up a blocked lumen at a site in the human (or even animal) body, for instance a coronary artery, aorta or the oesophagus etc. The occlusion might be caused for instance by a disease such as stenosis or by cancer. Stents preferably have a flexible structure allowing them to be collapsed to reduce their outer dimensions. This is to facilitate the passage of the stent into the site in the body where the stent is expanded for deployment. Typical uses of a stent are to open blocked coronary arteries and large veins, to treat obstructions to breathing in the trachea and bronchus, to allow the passage of urine in the prostate and, more recently, to palliate cancer stenosis in the oesophagus. Stent therapy is now widely accepted for interventional treatment not only in the vascular system, but also the gastrointestinal, belier and urinary systems. Stent techniques have come to be regarded as simply, safe and effective in comparison to other surgical or non-surgical treatments.

Known stents have one of five basic constructions that is tubular, coil, ring, multi-design and mesh structures. Tubular stents are rigid. The other types of known structures are collapsible and typically comprise an open tubular structure of structural elements which may be collapsed to facilitate deployment. The various known structures have different features and advantages, for example a high expansion rate, a high strength, good flexibility and/or good tractability. Whilst some structures provide different combinations of these advantages, an ideal stent sharing all these advantages has yet to be realised.

One of the major problems with known stents is restenosis occurring after implantation. This is a particular problem for mesh stents and other open structures as tissues grow through the stent and block the lumen again and is a particular problem in oesophageal applications. Some reports suggest that restenosis is due to cell damage occurring during deployment at the blocked site as the stent pushes against the cell wall. The amount of such damage is dependent on the stent configuration. After significant tissue growth through a stent, the stent cannot be retrieved. Thus it may be necessary to implant further stents after a first stent becomes blocked in order to reopen the blockage. As this involves stents being implanted inside one another, there is a limit to the number of stents which can be implanted at one location.

To overcome this problem, covered stents have been developed. Covered stents were developed by attaching a tubular flexible cover, for example of polyester, attached around the outside of a wire mesh stent structure. The use of such a cover around a wire mesh stent is an effective way to prevent restenosis. However, the common problems of covered stents include rupture of the cover and, when used in the oesophagus, for example, bolus obstruction, tumour ingrowth, gastro-oesophageal reflux, migration/slippage, and difficulties in delivery especially for high oesophaegeal malignancies and angulated cardio-oesophageal lesions. The risk of slippage and hence migration of the stent is a particular problem. Such covered stents still rely, for example, on a mesh frame for collapse and expansion during deployment, but there has been very little investigation of the integrated expanding mechanism when the stent is covered.

As a result of the problems described above for both covered and uncovered stents re-intervention is often required. As a result many patients have sub-optimal response to this type of treatment.

Current expandable stents are expensive to manufacture due to their complicated structures which are labourious to form. The high cost has reduced their widespread use. Particularly for the oesophagus, doctors often opt for cheaper, semi-rigid plastic tubular stents even though they carry a higher risk of oesophagus perforation than the expandable stents.

The present invention is intended to provide a stent which avoids at least some of the problems discussed above.

According to the present invention, there is provided a stent comprising a biocompatible sheet arranged as a tube folded with a pattern of folds allowing the stent to be collapsed for deployment.

Such a structure for a stent provides numerous advantages. As the stent is formed from a sheet, restenosis is prevented. Furthermore, the pattern of folds allows the stent to be collapsed for deployment facilitating delivery to the blocked site in the body. The pattern of folds may allow the tube to be collapsed both radially and longitudinally of the tube. Alternatively, the pattern of folds may only allow the tube to be collapsed radially. Longitudinal collapse is advantageous where the blocked site is particularly inaccessible. On the other hand, in many uses the medical practitioner finds it more convenient if there is no longitudinal collapse in order to judge the length of the deployed stent prior to deployment. For such uses, it is preferred to use a pattern of folds which has a reduced or zero longitudinal collapse.

The stent may also reduce slippage as compared to a known covered stent. Firstly, the folds may provide an uneven outer surface which reduces slippage. Secondly, the outer surface may be provided with a high degree of friction, for example by selection of the biocompatible material of the stent or by roughening the outer surface.

The use of a pattern of folds to collapse the stent allows it to be packaged compactly and to have good flexibility for ease of delivery to the blocked site. The structure can be simple in structural form and is hingeless which increases reliability. The design of the stent is generic, so it can be adapted for use at different anatomical sites. For example, by varying the diameter, length and/or bifurcation the stent may be collapsed for retrieval at a later date after implantation.

As the stent may be manufactured simply by folding a sheet, it is relatively simple to manufacture. This will minimise costs and it is anticipated that costs might be kept below many known expandable stents.

The stent is particularly useful for use in the oesophagus, where restenosis is a particular problem, or as a stent graft in the aorta. However, the stent may be used at any site in the body by appropriate sizing of the stent.

Many different patterns of folds are possible. Desirably, for ease of the design and manufacture wherein the pattern of folds comprises a unit cell repeated over at least a portion of the sheet, or the entire sheet.

In the preferred pattern of folds, wherein the unit cell comprises: an outer circumferential edge of hill folds comprising a pair of longitudinal edge folds extending along the tube and transverse edge folds extending around the tube; a central longitudinal fold extending along the tube between the transverse edge folds; and angular folds extending from each intersection of a longitudinal edge fold with a transverse edge fold to the central longitudinal fold. Many variations within this pattern are possible.

The choice of pattern may be selected to balance the ease of deployment, which generally improves as the degree of overlap in the folded pattern decreases, with the compactness of the stent when collapsed, which generally improves as the degree of overlap in the folded structure increases.

A particularly advantageous pattern is one which progresses helically around the tube. For example, the pattern of folds may include uninterrupted lines of folds progressing helically around the tube. Alternatively, the pattern of folds may comprise at least one row of unit cells progressing helically around the tube.

Such a helical pattern provides a number of advantages. Firstly, it can be folded more compactly in the longitudinal direction, because of the twist in the pattern, in comparison with a stent having a pattern of folds which does not progress helically.

Secondly, the stent with a helical pattern may be deployed more easily, because the collapse and expansion of the stent is synchronised. That is to say, the helical pattern causes the forces during collapse and expansion to be transferred along the tube. This may be envisaged as being caused by the force being transferred along uninterrupted lines of folds progressing helically around the tube. Consequently, collapse and expansion of the tube may be induced by the simple expedient of twisting the tube. As such a twist is easy to apply, this greatly improves the ease of deployment.

Thirdly, the helical pattern holds the stent in its expanded configuration.

In order that the present invention may be better understood, the following description of embodiments of the present invention is given by way of non-limitative example with reference to the accompanying drawings, in which:

FIGS. 5, 7, 12, 13, 15–19, 21–24, 26–31, 33 and 34 are diagrams of unit cells with alternative patterns of folds with the sheet in its unfolded state;

Figure 9:
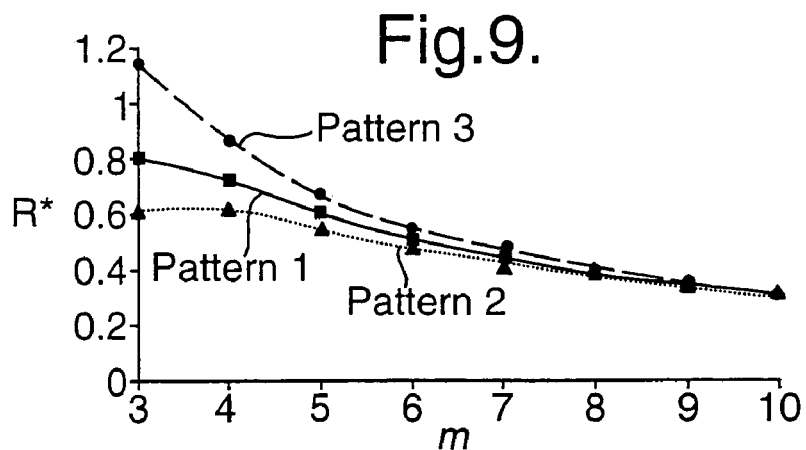
Figure 10:
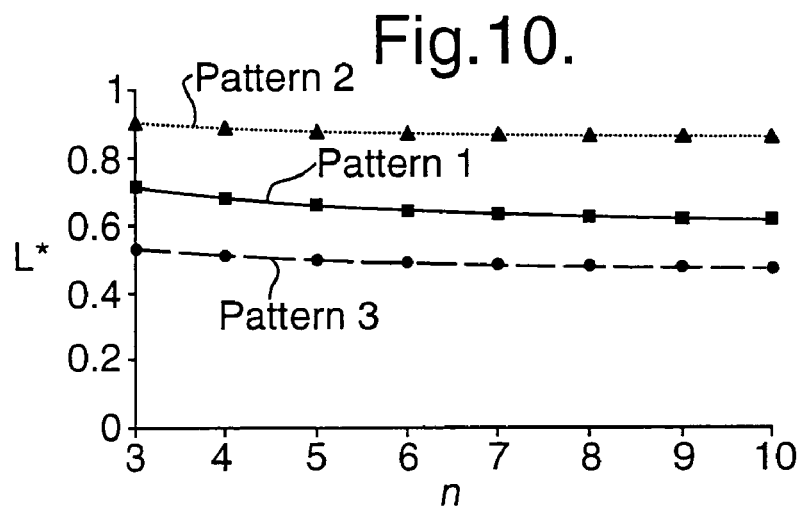
Figure 11:
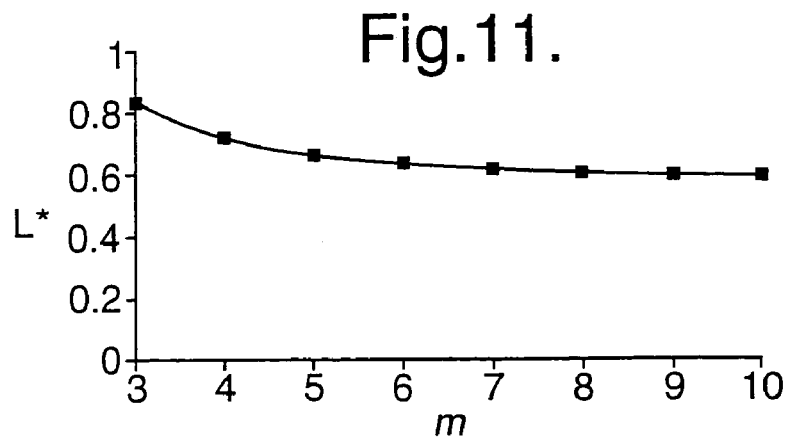
Figure 43:
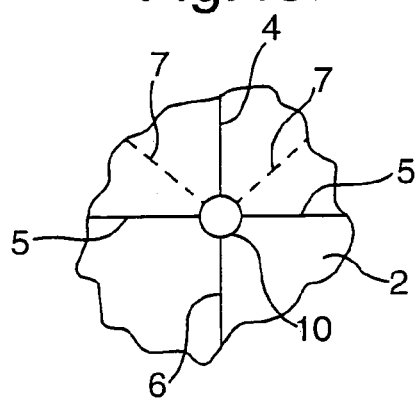

FIGS. 6, 8, 14, 20, 25, 32, and 35–42 are diagrams of sheets with alternative patterns of folds with the sheet in its unfolded state;

FIGS. 9 to 11 are graphs of the change in dimensions of a stent against the number of unit cells in the pattern of folds; and FIG. 43 is a view of a portion of a sheet of the stent showing an aperture at a node where folds intersect.

Figure 1:
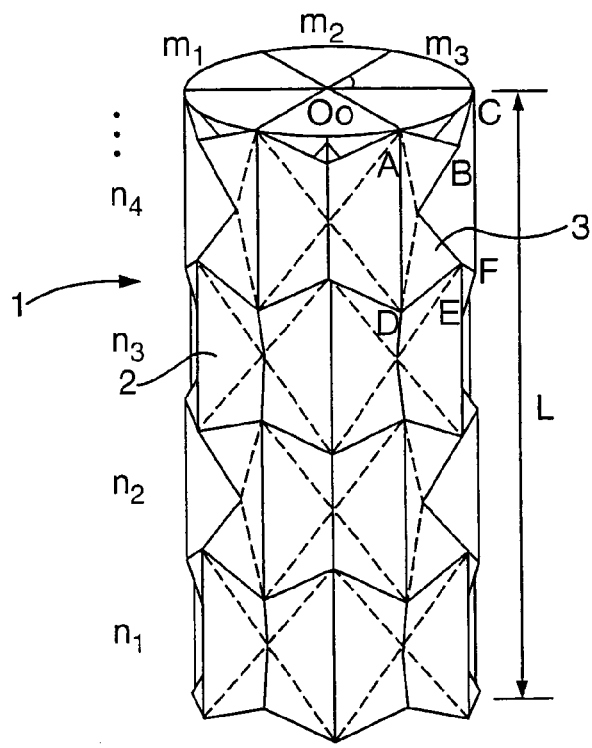
FIG. 1 is a perspective view of a stent using one of the folding patterns in accordance with the present invention.

A stent 1 in accordance with the present invention is illustrated in FIG. 1. The stent 1 comprises a biocompatible sheet 2. The sheet 2 is arranged as a tube with a pattern of folds which allow the stent to be collapsed for deployment.

The pattern of folds comprises a unit cell 3 which is repeated over the entire area of the sheet 2. The pattern of folds is illustrated more clearly in FIGS. 2 and 3 which are views of, respectively, the unit cell 3 and the unit cells developed over the sheet 2 in the unfolded state, notionally "unwrapped" from its tubular form, the lines a-a and b-b being the same line longitudinally along the tube. The unit cells 3 are in rows repeating around a direction perpendicular to the longitudinal axis of the tube.

Figure 2:
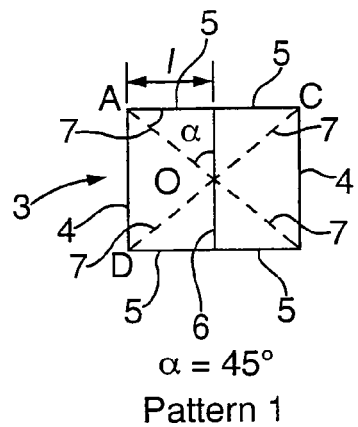
FIG. 2 is a diagram of a unit cell of a pattern of folds with the sheet in its unfolded state.
Figure 3:
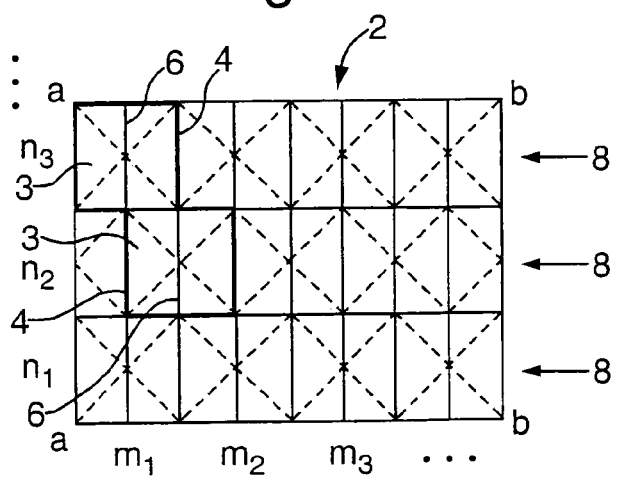
FIG. 3 is a diagram of the sheet with unit cell of FIG. 2 developed to form the overall pattern of folds with the sheet in its unfolded state.

In FIGS. 2 and 3, and indeed the further figures illustrating patterns of folds, the lines are fold lines where the sheet 2 is folded. Between the folds, the sheet 2 is flat or planar. Continuous and dashed lines indicate folds of first and second opposite types. The two types are valley and hill folds. Hill folds are folds which form a peak when viewed from the outer side of the tube. Valley folds are folds which form a valley when viewed from the outer side of the tube. In the following description, it will be assumed that the folds of the first type are hill folds and the folds of the second type are valley folds.

In general, the two types of fold are reversible in any given pattern, that is replacing all hill folds with valley folds and replacing all valley folds with hill folds. However, some patterns when reversed cause the tube to lock and hence do not allow the tube to be collapsed or expanded. The present invention contemplates the alternative that the folds of the first type are valley folds and the folds of the second type are hill folds, except when this causes locking of the structure.

For convenience, the pattern of folds illustrated in FIGS. 1 to 3 is referred to as Pattern 1.

The unit cell 3 comprises the following folds.

Unit cell 3 has an outer circumferential edge of hill folds. In particular, these are a pair of longitudinal edge folds 4 extending along the tube parallel to one another and transverse edge folds 5 extending around the tube.

The unit cell 3 further comprises a central longitudinal fold 6 extending along the tube between the transverse edge folds 5.

Lastly, the unit cell 3 has four angular folds 7 each extending from a respective intersection A, C, D or F of a longitudinal edge fold 4 with a transverse edge fold 5 to the central longitudinal fold 6. All four angular edge folds 7 intersect the central longitudinal fold 6 at the same position O. The length l of each transverse edge fold 5, that is from the intersection (e.g. at A) with a longitudinal edge fold 4 to a central intersection (e.g at B) with the central longitudinal fold 6, is equal to the length of the portion of the central longitudinal fold 6 from the central intersection (e.g. at B) with the transverse edge fold 5 to the intersection (e.g. at O) with an angular fold 7. Therefore, the triangle AOB and equivalent triangles within the unit cells 3 are isosceles triangles. The angle $\alpha$ (e.g. angle OAB) between a transverse edge fold 5 and an angular fold 7 is 45°.

The unit cell 3 is symmetrical about the central longitudinal fold 6 and about an imaginary line extending around the tube perpendicular to the central longitudinal fold 6 and intersecting the central longitudinal fold 6 at O.

The angular folds 7 are valley folds and the central longitudinal fold 6 is a hill fold. Accordingly, the unit cell 3 is folded as illustrated in perspective view in FIG. 1 where the intersections A to F of the various fold lines from FIG. 2 are indicated for one of the unit cells 3.

The unit cell 3 is repeated as illustrated in FIG. 3. In particular, the unit cells 3 are arranged in rows 8 labelled $n_1$, $n_2$, . . . , the rows repeating along the tube. The unit cells 3 of adjacent rows are offset, as illustrated by the unit cells 3 illustrated in bold outline in FIG. 3, that is with the longitudinal edge folds 4 of each row 8 meeting the central longitudinal folds 6 of the adjacent rows 8. The number n of rows 8 labelled $n_1$, $n_2$, . . . in FIGS. 1 and 3 and the number m of unit cells 3 within each row around the tube labelled $m_1$, $m_2$, . . . in FIGS. 1 and 3 can be freely varied. Similarly, the absolute dimensions of the sheet 2 and the unit cell 3 can be freely varied.

One of the interesting properties of Pattern 1 is that it causes the stent 1 to collapse and expand both longitudinally and radially. That is both the length of the tube and the radius of the tube increase during expansion and decrease during collapse. This property provides the advantage that the folded stent 1 can be packaged compactly. This makes the stent 1 easier to deliver through narrow passages of the body and facilitates deployment at a blocked site where it can be expanded.

Figure 4:
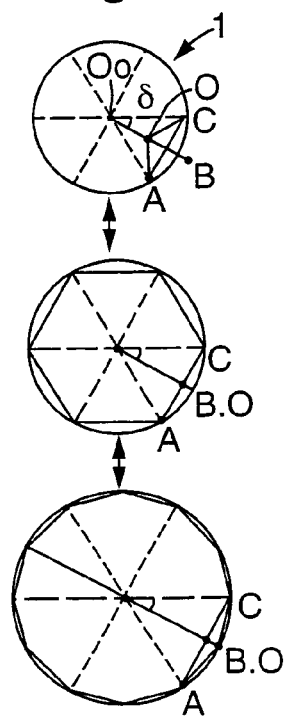
FIG. 4 is a progression of end views of the stent of FIG. 1 during expansion and contraction.

FIG. 4 is a progression of end views of the stent 1 during its expansion and contraction. As can be seen from FIG. 4, the central part of the unit cell 3 at the intersection (at O) of the angular fold 7 with the central longitudinal fold 6 moves inwardly and outwardly, causing a change in the radius of the stent 1 during deployment. This also causes a reduction in the distance between the intersections (at B and E) between the central longitudinal fold 6 and the transverse edge folds 5, which causes a change in the axial length L of the stent 1.

Further possible patterns of folds will now be described. The further patterns of folds are variations on Pattern 1 shown in FIGS. 1 to 3. For clarity and for brevity, the further patterns will all be described by explaining the variations from Pattern 1 without repeating the common features. The same reference numerals as for Pattern 1 will be used to denote the sheet 2, the unit cell 3, the equivalent folds 4 to 7 and the rows 8.

Figure 5:
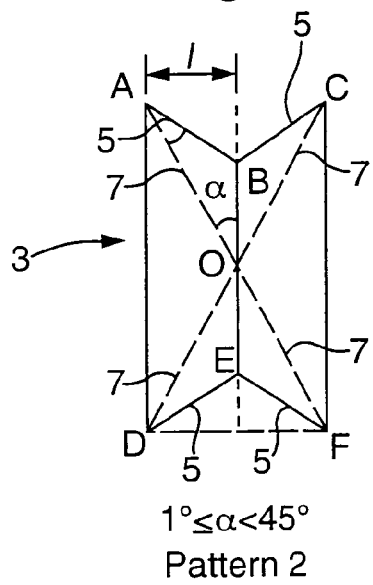
Figure 6:
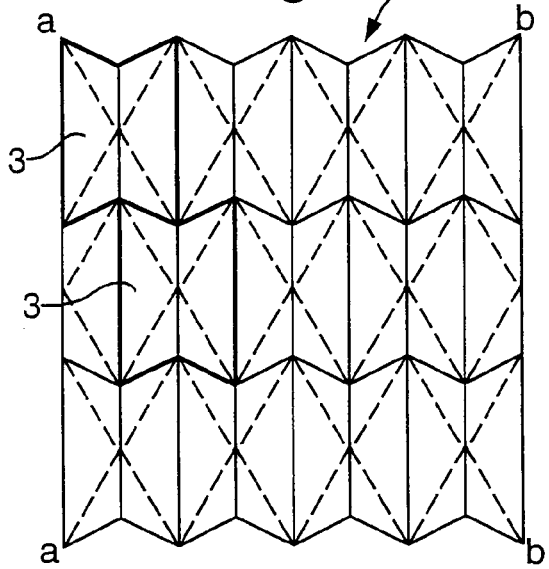

Pattern 2 is illustrated in FIGS. 5 and 6. FIG. 5 is a diagram of the unit cell 3 and FIG. 6 is a diagram of the sheet with the unit cell 3 developed across the sheet 2. Pattern 2 is similar to Pattern 1 except that the angle α (e.g. angle OAB) between each transverse edge fold 5 and angular fold 7 is less than 45°, so the unit cell 3 is no longer rectangular.

Figure 7:
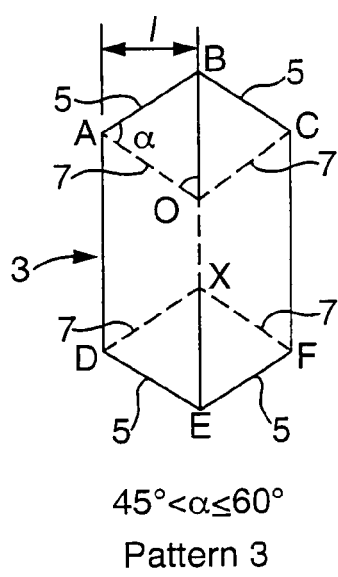
Figure 8:
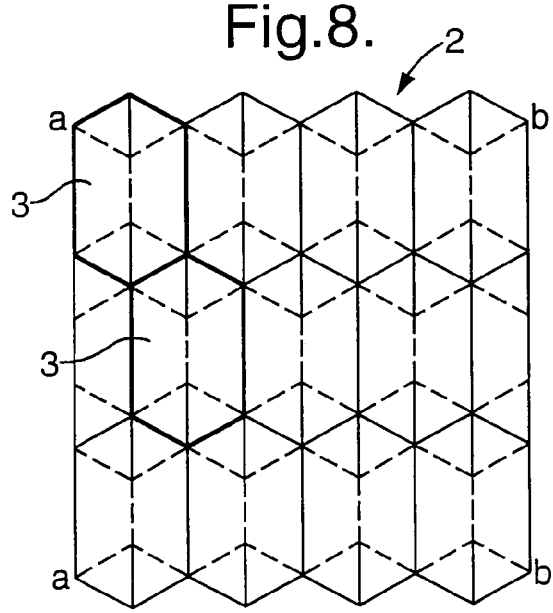

Pattern 3 is illustrated in FIGS. 7 and 8. FIG. 7 is a diagram of the unit cell 3 and FIG. 8 is a diagram of the sheet 2 with the unit cell 3 developed across the sheet 2.

Pattern 3 varies from Pattern 1 in that the angle α (e.g. angle OAB) between each transverse edge fold 5 and in respect of angular fold 7 is greater than 45° and less than or equal to 60°. As a result the shape of the unit shape 3 becomes a polygon. The angle a should be equal to or less than 60° to allow folding of the sheet 2.

Pattern 3 also varies from Pattern 1 in that the angular folds 7 do not all intersect the central longitudinal fold 6 at the same position. Instead, for each pair of angular folds 7 at opposite longitudinal ends of the unit cell 3, the pair of angular folds 7 intersect the central longitudinal folds 6 at the same position, but the pairs of angular folds 7 intersect the central longitudinal fold 6 at separated positions O and X. Between these separated positions O and X, the central longitudinal fold 6 is a valley fold. However, the portions of the central longitudinal fold 6 extending from a central intersection (at B or E) with a respective one of the transverse edge folds 5 to a respective intersection (at O or X) with the angular folds 7 remain as hill folds. The separation between the intersections (at O and X) of each pair of angular folds 7 and the central longitudinal fold 6 may be freely varied. This separation may be reduced to zero (as in Patterns 1 and 2), but the longitudinal length of the unit cell 3, or more particularly the length of the central longitudinal fold 6, may not be further reduced or else folding is prevented.

To understand and compare the folding of Patterns 1 to 3, the geometric properties of Patterns 1 to 3 have been analysed as follows. The analysis is based on Pattern 2 with the angle α as 30° and on Pattern 3 with the angle α as 60°.

Firstly, the ratio R* of the outer radius of stent 1 (ie the distance from Oo to A or B) in its fully folded configuration to the outer radius of the stent 1 in its fully deployed configuration was calculated for stents 1 having differing numbers m of unit cells 3 in each row 8 of the sheet 2 around the tube. The relationship between R* and m for Patterns 1, 2 and 3 is illustrated in FIG. 9 where Pattern 1 is shown by a continuous line, Pattern 2 is shown by a dotted line and Pattern 3 is shown by a dashed line.

For each model, it will be noted that the value of R* decreases as the number m of unit cells 3 in each row 8 increases. In other words, a large value of m makes the pattern fold more compact in the radial direction. Thus the number m of unit cells 3 in each row 8 around the tube is preferably large to minimise the radius of the stent 1 on collapse. However, increasing the number m of unit cells 3 in each row 8 causes the folding to become complex and potentially affected by the thickness of the material of the sheet 2. The number m of unit cells 3 in each row 8 should be selected to balance these two factors.

It will also be noted from FIG. 9 that as compared to Pattern 1, Pattern 2 has a lower value of R* and hence folds more compactly, whereas Pattern 3 has a higher value of R* and hence folds less compactly. However, the difference in the value of R* between Patterns 1, 2 and 3 becomes small when m is larger than 9. When m=10 the radius of the stent 1 in its fully folded configuration is about 30% of that in its fully deployed configuration, for each pattern.

Also, the value L* of the ratio of the total length of the stent 1 in its fully folded configuration to the length of the stent 1 in its fully deployed configuration was calculated for different values of the number m of unit cells in each row 8 of the sheet 2 around the tube and for differing values of the number n of rows 8 along the tube.

FIG. 10 shows the value of L* for each of Patterns 1 to 3 for differing values of n when m=6. In FIG. 10, Pattern 1 is shown by a continuous line, the Pattern 2 is shown by a dotted line and Pattern 3 is shown by a dashed line. It will be seen that for each model, the ratio L* slowly decreases as n increases. This means that all three Patterns fold more compactly in the longitudinal direction as the number n of rows 8 of unit cells 3 increases. The value of L* becomes nearly constant when n is greater than 7, so there is no particular benefit in increasing the number n of unit cells 3 above about 7.

It will be noted that, as compared to Pattern 1 in the longitudinal direction, Pattern 3 folds more compactly, whereas Pattern 2 folds less compactly but maintains flexibility. Therefore, pattern 3 is preferred for uses where longitudinal collapse is desirable to allow access of the stent 1 to the blocked site, whereas Pattern 2 is preferred for uses where the medical practitioner prefers the longitudinal collapse to be minimised.

FIG. 11 shows the value of L* for Pattern 1 for different values of m when n=7. It will be noted that L* becomes smaller as m increases. Thus increasing m reduces the longitudinal collapse of the stent 1 when folded, as well as reducing the radial collapse.

Figure 12:
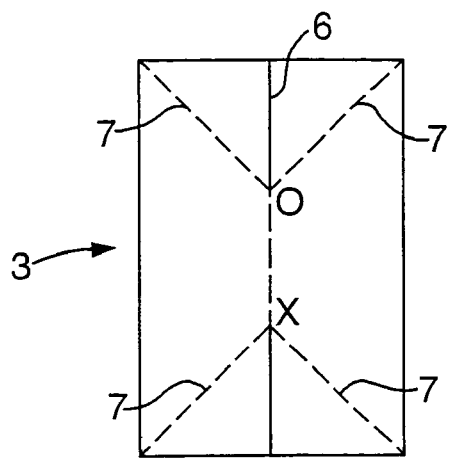
Figure 13:
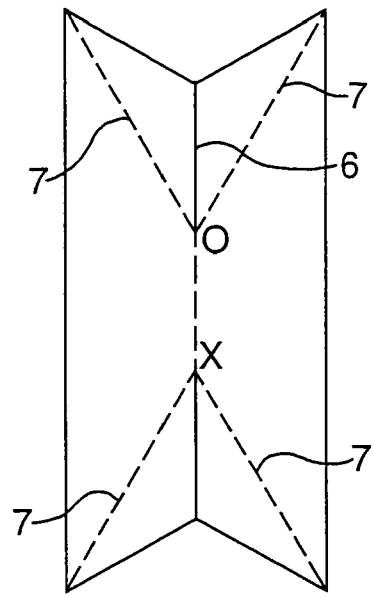
Figure 14:
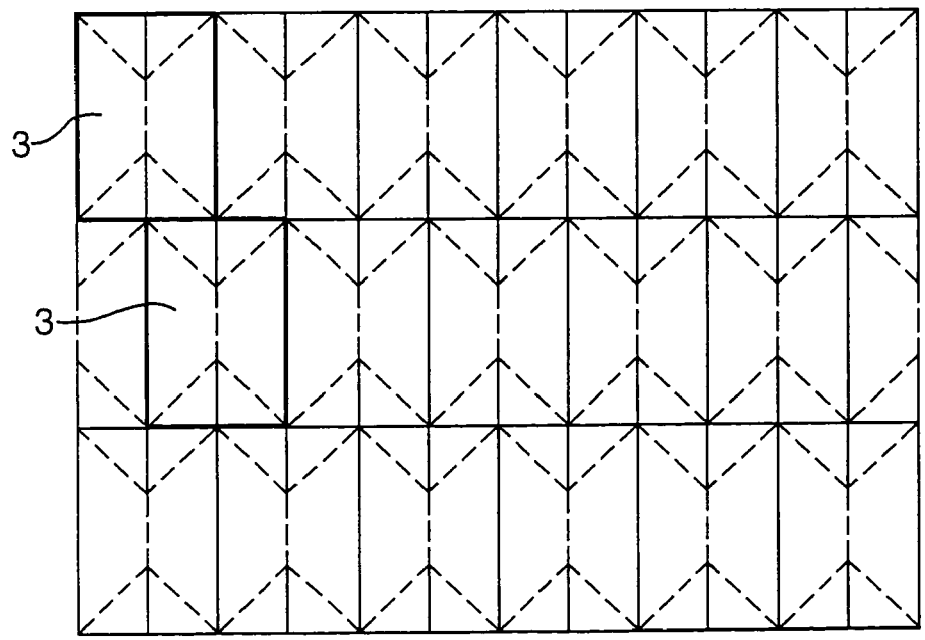
Figure 15:
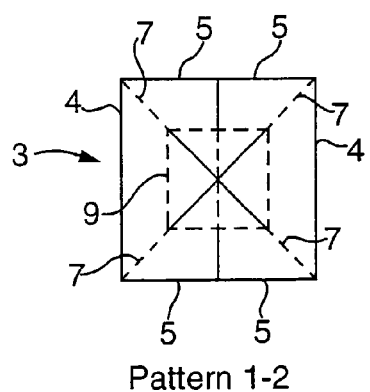
Figure 16:
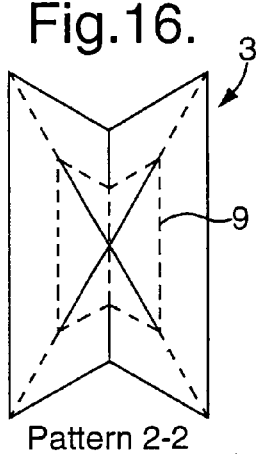
Figure 17:
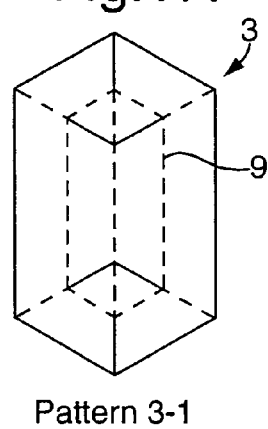
Figure 18:
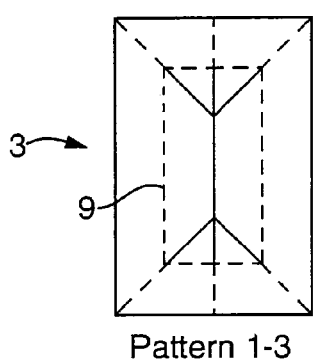
Figure 19:
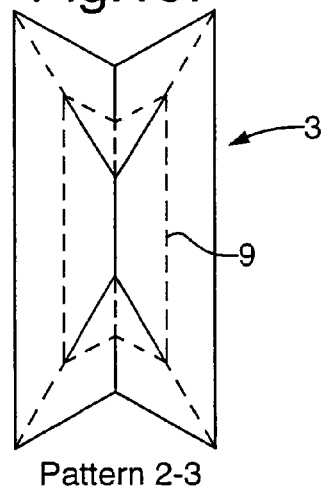

FIGS. 12 and 13 are diagrams of the unit cells 3 of the Patterns 1-1 and 2-1 which are variations of Patterns 1 and 2, respectively. FIG. 14 is a diagram of Pattern 1-1 developed across the sheet 2. In both cases, the length of the unit cell 3 is increased so that the pairs of angular folds 7 intersect the central longitudinal fold 6 at separated positions O and X between which the central longitudinal fold 6 is a valley fold.

Figure 20:
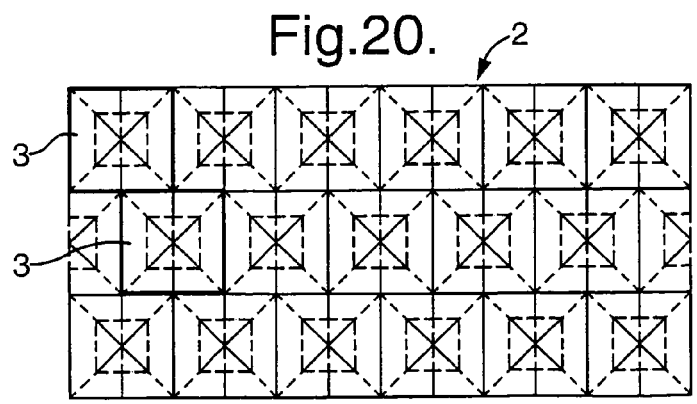
Figure 21:
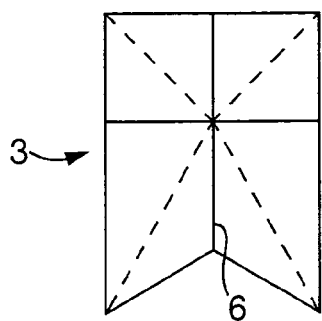
Figure 22:
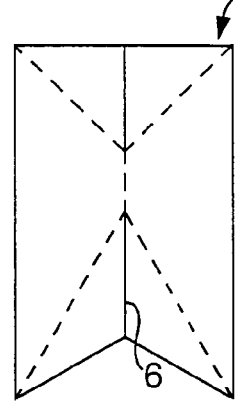
Figure 23:
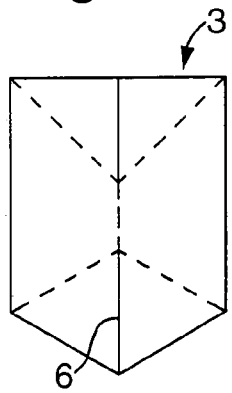
Figure 24:
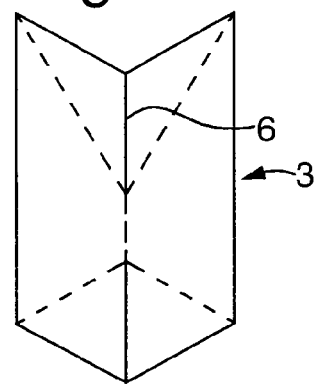

FIGS. 15 to 19 are diagrams of the unit cell 3 of Patterns 1-2, 2-2, 3-1, 1-3 and 2-3, respectively, which are themselves variations of models 1, 2, 3, 1-1 and 2-1, respectively. FIG. 20 is a diagram of Pattern 1-2 with the unit cell 3 developed across the sheet of material 2. In each case, the variation is to provide an additional ring of valley folds 9. Each valley fold 9 extends parallel to an adjacent longitudinal or transverse edge fold 4 or 5. The valley folds 9 extends between an angular fold 7 and either another angular fold 7 or else the central longitudinal fold 6. The ring of valley folds 9 causes the surface of the unit cell 3 to be folded twice. Therefore inside the ring of valley folds 9, the folds of the basic unit cell 3, that is the angular fold 7 and the central longitudinal fold 6, reverse. That is to say, hill folds reverse to valley folds and valley folds reverse to hill folds. Such a ring of valley folds 9 has the advantages that the double folding pattern causes the inner surface of the sheet 2 inside the tube to become smoother and allows the unit cell 3 to be folded more compactly, because the peak point O of the unit cell 3 in its folded state shown in FIG. 4 is folded inside points A and C of the folded unit cell 3, ie allowing the unit cells 3 to be folded compactly in the radial direction.

Figure 25:
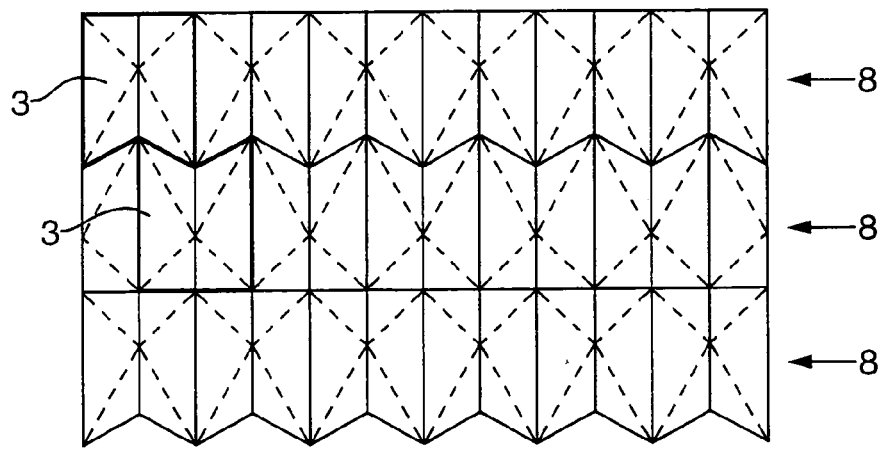
Figure 26:
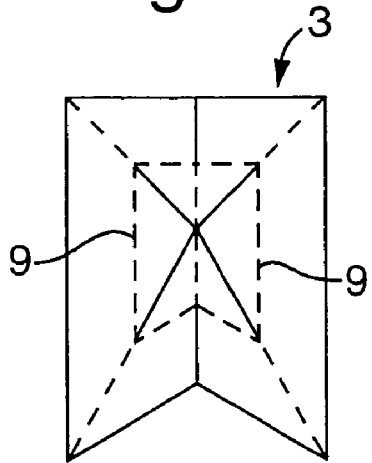
Figure 27:
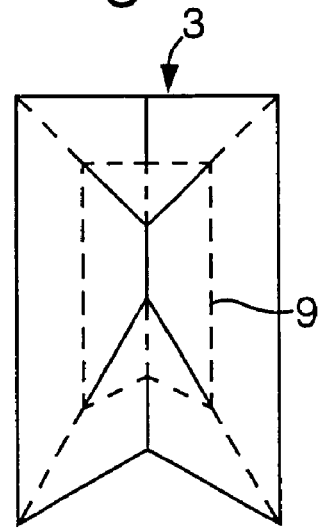
Figure 28:
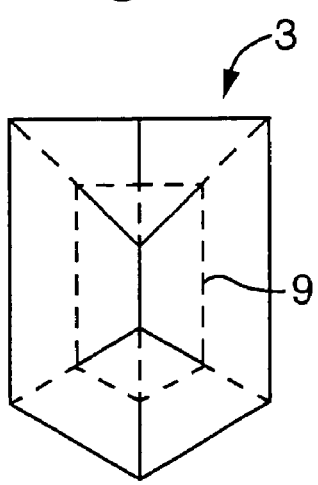
Figure 29:
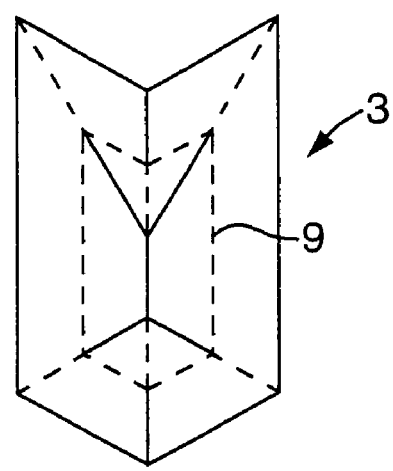

The unit cells 3 described above are symmetrical both about the central longitudinal fold 6 and also about an imaginary line extending around the tube perpendicular to the central longitudinal fold 6. However, this is not essential. Either or both degrees of symmetry may be removed. For example FIGS. 21 to 24 are diagrams of Patterns 4-1 to 4-4, respectively, which are symmetrical only about the central longitudinal fold 6. FIG. 25 is a diagram of Pattern 4-1 with the unit cell 3 developed over the sheet 2. Accordingly, the unit cell 3 of alternate rows 8 is reversed in the longitudinal direction. This may also be viewed as a Pattern having a larger unit cell comprising the two unit cells 3 illustrated in FIG. 21 in bold outline combined together. Patterns 4-1 to 4-4 may also be viewed as consisting of the other half of one of the Patterns described above with the lower of another of the Patterns described above. For example, Pattern 4-1 may be viewed as the upper half of Pattern 1 combined with the lower half of Pattern 2, and so on.

FIGS. 26 to 29 are diagrams of the unit cell 3 of Patterns 5-1 to 5-4, respectively, which are variations of Patterns 4-1 to 4-4, respectively, the variation is that the unit cell 3 further comprises a ring of valley folds 9 as in Patterns 1-2, 2-2, 3-1, 1-3 and 2-3.

FIGS. 30 and 31 illustrate Patterns 6-1 and 6-2 which are symmetrical only about an imaginary line extending around the tube. These Patterns may also be viewed as combinations of longitudinally-extending halves of different Patterns described above, except that the central longitudinal fold 6 extends at an angle to the longitudinal direction along which the longitudinal edge folds 4 extend. In particular, if the angle BAO is $\alpha_1$, and then the angle BCO is $\alpha_2$, then the angle AOB is $\alpha_2$, the angle BOC is $\alpha_1$, and both angles ABO and CBO are $(\pi - \alpha_1 - \alpha_2)$. For example, Pattern 6-1 may be viewed as the combination of the left half of Pattern 1 with the right half of Pattern 2. Similarly, Pattern 6-2 may be viewed as the combination of the left half of Pattern 2-1 and the right half of Pattern 3.

Unlike the previous patterns, Pattern 6-2 cannot be used by itself, but must be combined with another pattern. For example, FIG. 32 is a diagram of Pattern 6-2 with the unit cell 3 developed over a sheet 2 and combined with Pattern 3. To enable the unit cells to fit together, alternate unit cells 3 of Pattern 6-2 along each row 8 are longitudinally reversed and a unit cell of Pattern 3 is arranged between successive pairs of unit cells 3 of Pattern 6-2, between the longer longitudinal edges of the unit cells 3 of Pattern 6-2. Thus, a larger unit cell is formed by the combination of two unit cells 3 of Pattern 6-2 with a unit cell of Pattern 3.

Figure 33:
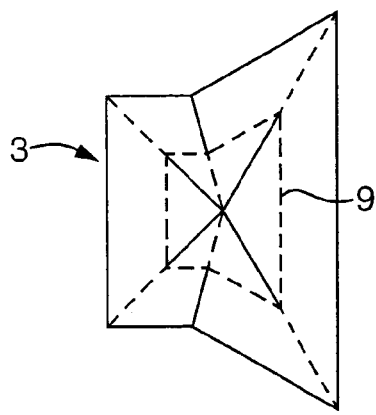
Figure 34:
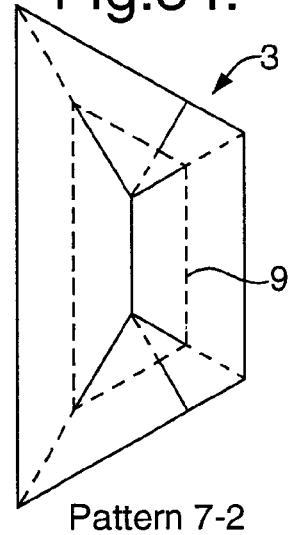

FIGS. 33 and 34 are diagrams of the unit cell 3 of Patterns 7-1 and 7-2 which are variations of Patterns 6-1 and 6-2. The variation is the addition of a ring of valley folds 9 similar to the valley folds 9 of Patterns 1-2, 2-2, 3-1, 1-3 and 2-3.

Figure 37:
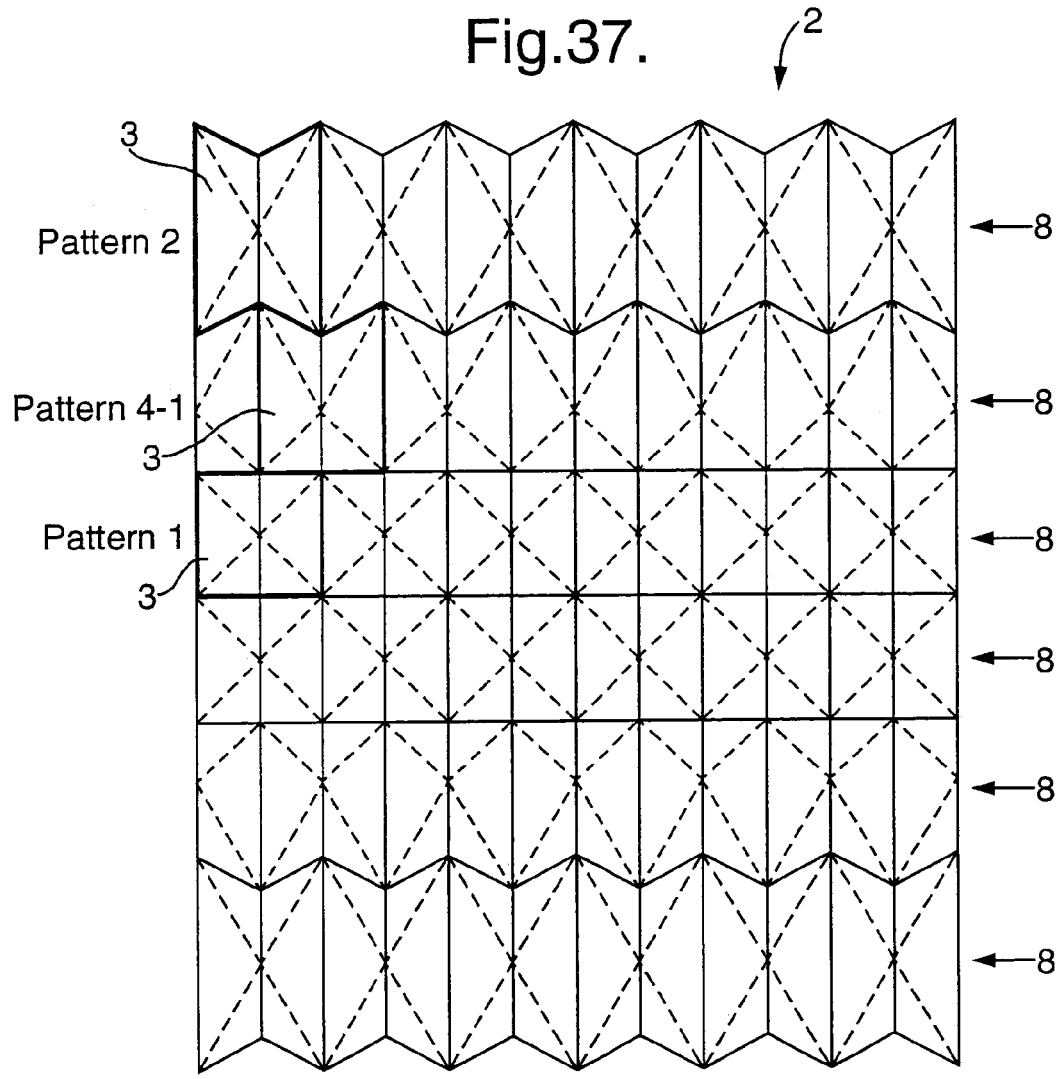
Figure 35:
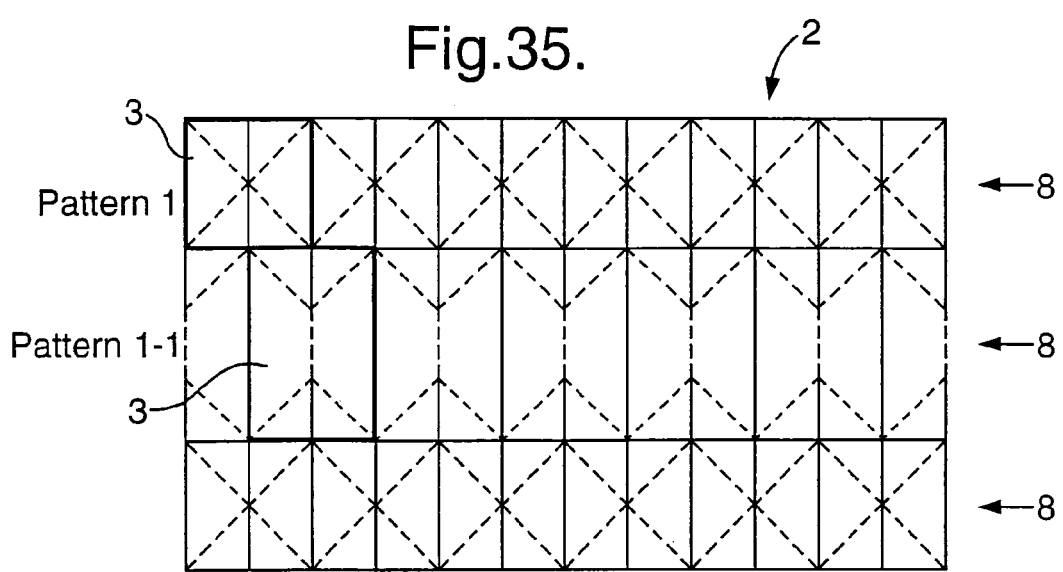
Figure 36:
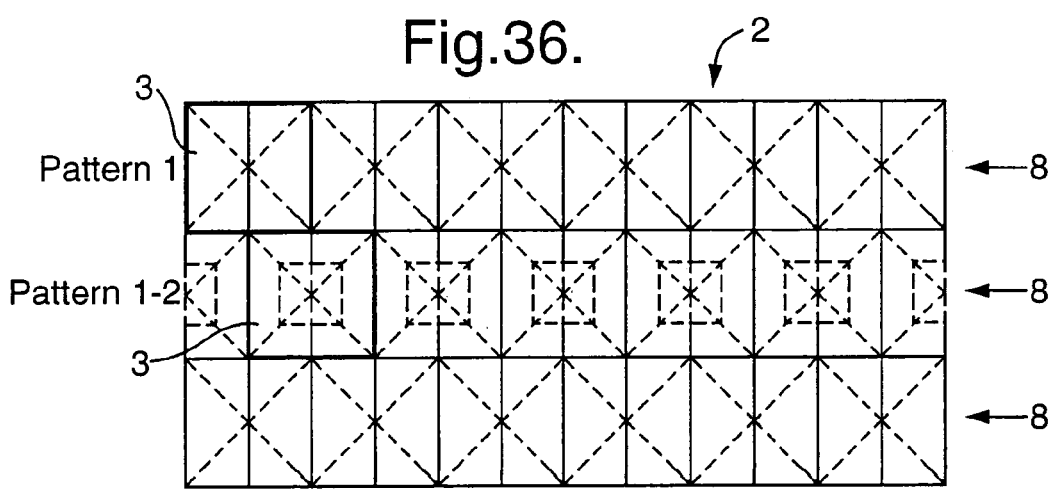
Figure 38:
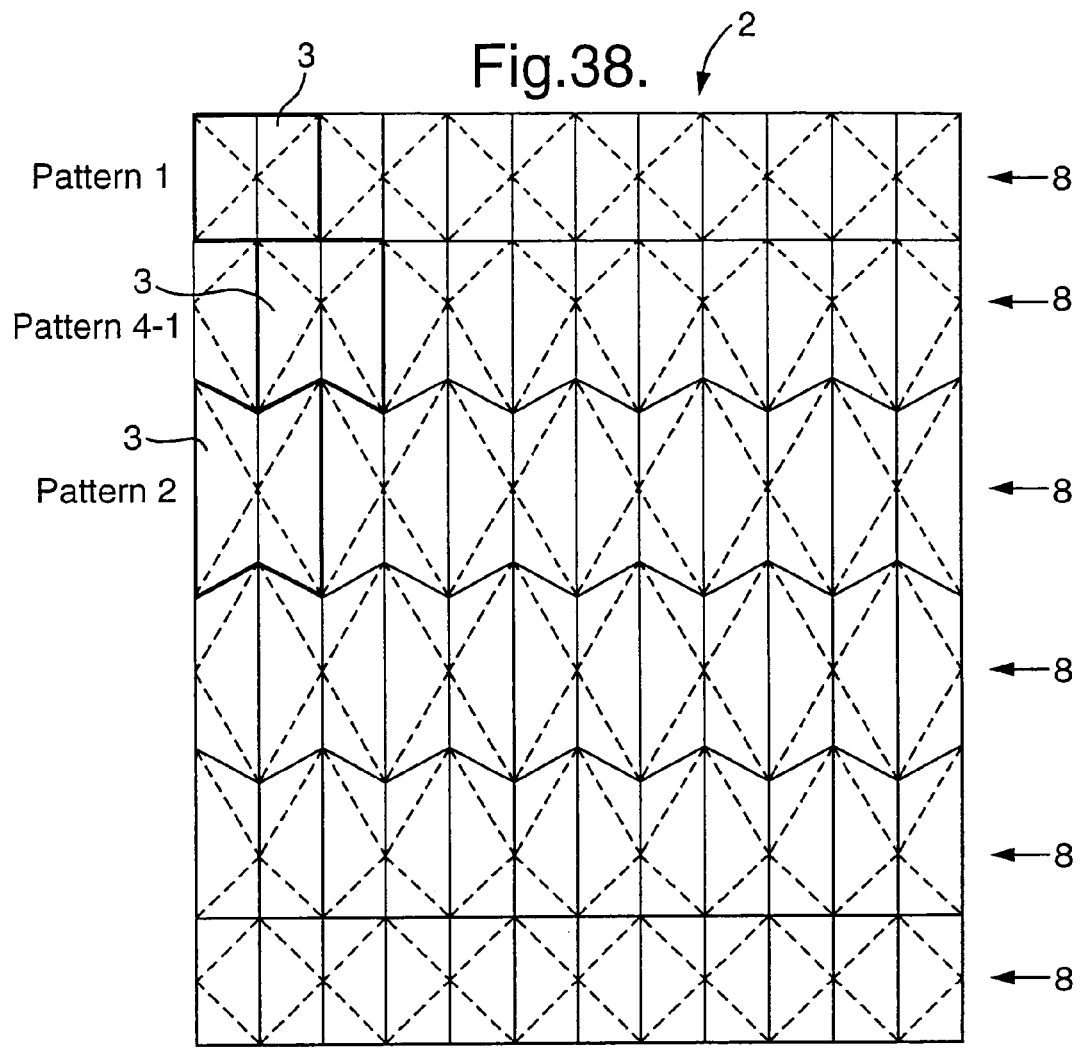

In the Patterns described above, a single unit cell 3 is repeated over the entire sheet, but this is not essential. In fact, different unit cells 3 may be repeated over different portions of the sheet 2. For example, FIGS. 35 to 39 show patterns of folds in which different rows 8 comprise a respective, different unit cell 3 repeated around the tube. In FIGS. 35 and 36, two different patterns are used. In FIG. 35, Patterns 1 and 1-1 are used for alternate rows. In FIG. 36, Patterns 1 and 1-2 are used for alternate rows. In FIGS. 37 and 38, three different patterns are used. In particular, in both FIGS. 37 and 38 unit cells 3 of Patterns 1, 4-1 and 2 are used for different respective rows 8, although in a different order longitudinally along the tube.

Figure 39:
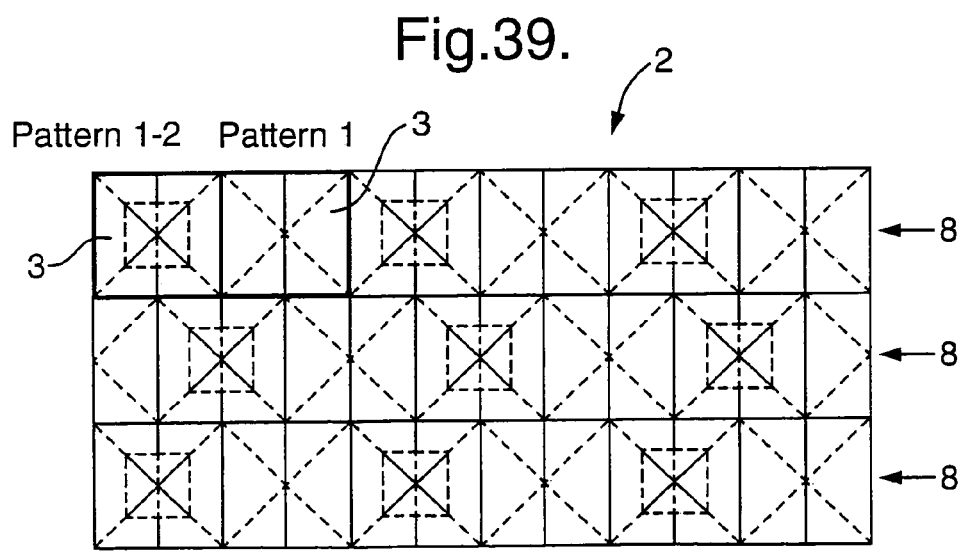
Figure 40:
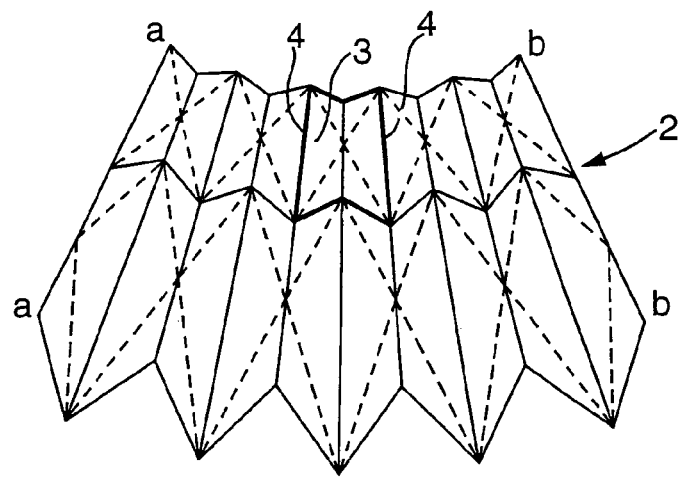

Similarly, FIG. 39 is a diagram of a pattern of folds in which each row 8 comprises two different unit cells 3 alternating along the row 8, in particular the unit cells of Patterns 1 and 1-2.

The patterns of folds described above produce a tube which is generally cylindrical by means of the unit cells 3 being arranged with parallel longitudinal edge folds 4 and has the same radius along the length of the tube. However, this is not essential. For example, the sheet 2 may be arranged in a tube which is conical along the entire length or along a portion thereof. This may be achieved using the pattern of folds illustrated in FIG. 40 which is based on a unit cell 3 of Pattern 2, but in which the unit cells 3 are of different sizes with the longitudinal edge folds 4 being angled relative to one another, instead of parallel. Therefore the longitudinal edge folds 4 are also angled with respect to the longitudinal direction of the tube. As a result, the sheet 2 of FIG. 40 forms a conical (or frustoconical) tube when folded. Alternatively, the tube may have a more complicated structure, for example having plural tubular portions branching off from a common node.

Figure 41:
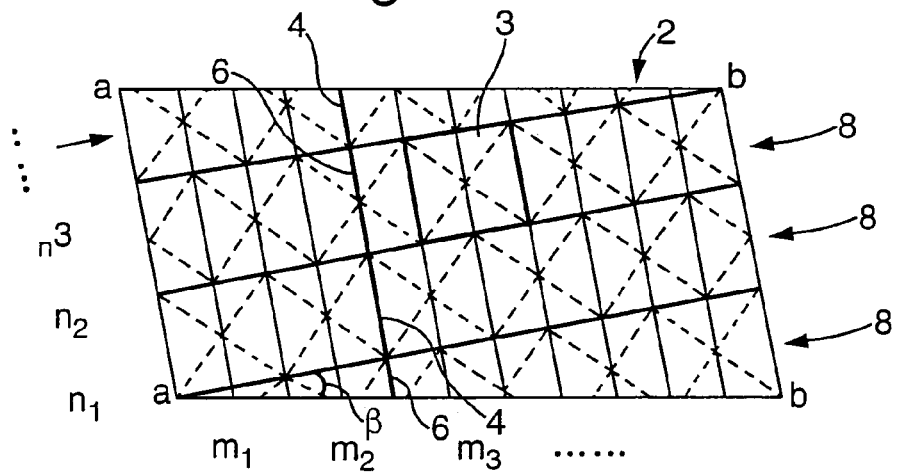
Figure 42:
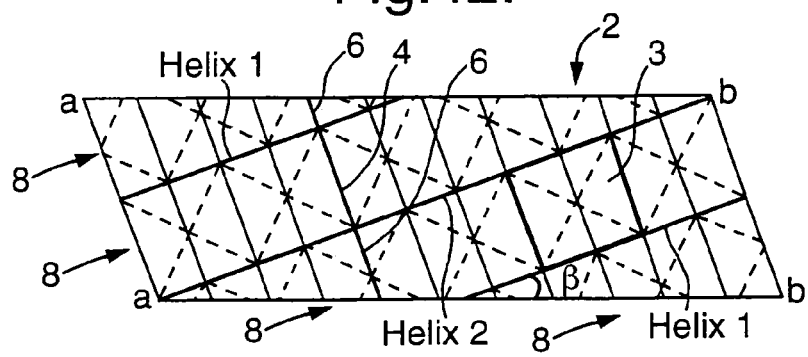

FIGS. 41 and 42 are diagrams of patterns in which unit cells 3 are arranged on the sheet 2 in rows 8 which progress helically around the tube when the sheet 2 is folded. FIGS. 41 and 42 are based on a unit cell of Pattern 1, but any of the patterns described above could alternatively be used. Consequently, the rows 8 of unit cells are arranged at a pitch angle or helix angle $\beta$ which is the angle between the direction in which the unit cells repeat and plane perpendicular to the longitudinal axis of the tube. When the sheet 2 is folded with the opposite lines a—a and b—b in FIG. 41 and 42 being the same line, successive rows 8 of unit cells 3 join end-to-end to form a longer row which progresses helically around the tube. In the pattern of FIG. 41, the angle x is selected so that the rows 8 combine to form a single row progressing helically around the tube. In the pattern of FIG. 42, the angle $\beta$ is selected so that the rows 8 join together to form two rows progressing helically around the tube.

As a result of the helical pattern it will also be noted that the longitudinal edge folds 4 and the central longitudinal folds 6 of alternate rows 8 meet together to form an uninterrupted fold line which also progresses helically around the tube.

Such a helical structure provides a number of advantages. Firstly, it allows the sheet 2 to be folded compactly in the longitudinal direction because of its capability of torsion. Secondly, the helical pattern assists with deployment, because the expansion and collapse of the sheet 2 is usually synchronised over the area of the sheet 2. That is to say, the helical progression of the pattern of folds spreads the force causing expansion or collapse to be transmitted along the length of the tube. This may be viewed as the force being transmitted along the uninterrupted lines of folds formed by the longitudinal edge folds 4 and the central longitudinal folds 6 of alternate rows 2 which progress helically around the tube. This means that a twist applied to the stent 1 can be used to generate expansion or collapse of the stent 1 which greatly assists deployment because a twist is simple to perform. Thirdly, the helical structure holds the stent 1 in its expanded configuration. This is because collapse of the stent requires torsional forces which are not usually developed at sites in the body.

The patterns described above are preferred because of their simplicity and hence ease of design and manufacture. However a stent in accordance with the present invention may be formed using numerous other patterns of folds which allow radial collapse and optionally longitudinal collapse. Alternative patterns may be regular or irregular and the sheet between the folds may in general be flat or curved.

The stents described above may be combined together to form a larger product or may have additional components added thereto.

Manufacture of a stent 1 in accordance with the present invention will now be described.

First, the biocompatible sheet 2 is provided.

The sheet may initially be planar, in which case opposed edges of the sheet are subsequently joined together to form a tube. In this case, in the drawings, the lines a-a and b-b may represent edges of the sheet 2 which are joined together. Alternatively, the sheet 2 may be manufactured be formed as a tube ab initio, that is with the sheet being continuous around the tube. In this case, in the drawing, the lines a-a and b-b are the same imaginary line along the length of the tube. This latter alternative has the advantage of avoiding the need to join the edges of a planar sheet but makes it harder to form the folds.

In its most simple form, the sheet 2 is a sheet of biocompatible material. Any biocompatible material may be used. Generally, a biocompatible material is selected with appropriate mechanical properties for the site at which the stent 1 is to be used. The material should be selected to be sufficiently rigid to hold its shape between the folds when implanted in a lumen. This is to perform its basic function of holding the lumen open. This must be balanced against the ease of folding the sheet and the need for the collapsed stent 1 to be sufficiently flexible to allow delivery to the blocked site.

Suitable materials for the sheet 2 include stainless steel or a shape memory alloy such as Nitinol. It is also anticipated that many polymers would be suitable.

The sheet 2 is desirably selected so that the outer surface of the sheet 2 on the outside of the tube provides a sufficient degree of friction to provide anchorage at the anatomical site where it is to be implanted. This may be achieved by selecting a material providing an appropriate degree of friction or by roughening the outer surface.

Alternatively, the sheet 2 may be a multi-layer material. In that case, the inner and outer layers may be selected to provide appropriate degrees of friction. Desirably the outer surface of the sheet 2 on the outside of the tube provides a higher degree of friction than the inner surface of the sheet 2 of the inner side of the tube.

In another form, the sheet 2 may have a coating of a biocompatible material.

The sheet 2 is folded with the desired pattern of folds. This may be achieved by initially forming fold lines which facilitate subsequent folding. For example, the fold lines may be formed by scoring the sheet or by stamping the sheet from both sides by stamps having ridges along the fold lines, the stamp on one side having the pattern of hill folds the other side having the pattern of valley folds.

However the preferred techniques to form fold lines are laser lithography and chemical etching.

In the case of laser lithography, a laser is used to form scores in the surface of the sheet 2 along the fold lines. The laser equipment for such processing is in itself conventional.

In the case of chemical etching, the sheet 2 is first masked by a material resistant to a chemical enchant, except along the desired pattern of folds. Then the etchant is applied to the sheet to etch scores in the pattern of folds where the masking material is not present. Subsequently the masking material is removed. Such a chemical etching process in itself is conventional. Preferably, a conventional photolithographic technique is used. In such a case, the masking material is a positive or negative photoresist applied across the entire sheet. Ultra-violet light is applied in an image of the pattern of folds, being positive or negative image for the case of a positive or negative photoresist, respectively. This alters the photoresist allowing it to be removed by the etchant in the pattern of folds, but leaving it resistant to the etchant elsewhere.

In general, the etchant and the masking material may be chosen having regard to the material of the sheet 2. However, particular possibilities are as follows.

In the case of a chemical etching of a sheet 2 of stainless steel, one possibility is to use the negative etching technique commonly used for etching stainless steel, for example using ferric chloride and 1% HCl as the etchant and using a dry film as a negative photoresist.

In the case of chemical etching of a sheet 2 of shape memory alloy, the following positive etching technique has been applied using a positive photoresist layer of solid contented HRP 504 or 506 as the masking material and using a mixture of hydrofluoric and nitric acid as the etchant. The etching method was applied to a sheet 2 of thickness 80 µm and size 80 mm×80 mm which was cleaned to improve the adhesion of the masking material. The masking material was applied by dip coating at a speed of 6 mm/min to create a coating of thickness 12 µm. The sheet 2 was then soft-baked at 75° for 30 minutes. The masking material was then exposed by UV light with a positive image of the pattern of folds on both sides of the sheet, and the image developed using PLS1: $H_2O$=1:4. Finally the sheet 2 was hard-baked at 120° for 60 minutes. The sheet 2 was then etched using a mixture of hydrofluoric acid and nitric acid in proportions HF 10%, $HNO_3$ 40%, $H_2O$ 50% or HF:$HNO_3$:$H_2O$=1:1:2 or 1:1:4.

Other ways to chemically etch a sheet 2 of shape memory alloy are negative etching with a rubber-type of photoresist or electrochemical etching with $H_2SO4/CH_3OH$, for example as disclosed in Eiji Makino, et al., "Electrochemical Photoetching of Rolled Shape Memory Alloy Sheets for Microactuators", Vol. 49, No. 8, 1998; and D M Allen, "The Principles and Practice of Photochemical Machining and Photoetching", Adam Hilger, 1986.

In the case of a sheet 2 which is initially planar, after folding the edges of the folded sheet 2 are joined together to form the sheet 2 into a tube.

As the stent is folded from a sheet 2, it is possible to manufacture it relatively cheaply. It is anticipated that manufacturing costs may be kept below current costs of many existing expandable stents.

The dimensions of the sheet 2, the type of pattern of folds and the dimensions of the unit cell 3 within the pattern of folds are selected based on the site at which the stent is intended to be used. The stent 1 may be used for treatment at sites in any type of lumen in the body simply by choice the dimensions and mechanical properties of the sheet of the stent 1. Once deployed, the stent 1 prevents restenosis, because it is formed from a sheet 2 which is effectively continuous. The stent 1 is particularly advantageous for use in the oesophagus where restenosis is a particular problem.

The stent 1 is used in the same manner as known stents, that is by initially collapsing the stent 1 to deliver the stent 1 to the site to be treated and subsequently expanding the stent 1. Manipulation of the stent 1 is performed using conventional medical techniques.

A potential problem with the stent 1 as described above is that high stresses are developed at the nodes where the folds 4 to 7 intersect. Such stresses could create weakness at the nodes, potentially causing sheet 2 to puncture or rip. To avoid this problem, aperture 10 may be formed in the sheet 2 at the nodes where the folds 4 and 7 intersect, or at least at those nodes where high stresses are likely to be developed.

An example of such an aperture 10 formed in a sheet 2 at the node where the longitudinal edge folds 4, the transverse edge folds 5 and the angular fold 7 intersect is shown in FIG. 43. The aperture 10 in FIG. 43 is shown as being circular, but may be of any shape. The aperture 10 is sufficiently small that it does not allow significant in-growth through the aperture 10, hence effectively retaining the continuous nature of the sheet 2.

The invention claimed is:

1. A stent comprising a biocompatible sheet arranged as a tube folded with a pattern of folds allowing the stent to be collapsed for deployment, the pattern of folds comprising a unit cell repeated over at least a portion of the sheet, the unit cell comprising:
an outer circumferential edge of folds of a first type comprising a pair of longitudinal edge folds extending along the tube and transverse edge folds extending around the tube;
a central longitudinal fold extending along the tube between the transverse edge folds; and
angular folds extending from each intersection of a longitudinal edge fold with a transverse edge fold to the central longitudinal fold.

2. A stent according to claim 1, wherein for each pair of angular folds at opposite longitudinal ends of the unit cell, the pair of angular folds intersect the central longitudinal fold at the same position.

3. A stent according to claim 2, wherein the lengths of:
a transverse edge fold from the intersection with a longitudinal edge fold to a central intersection with the central longitudinal fold; and
the portion of the central longitudinal fold from said central intersection with the transverse edge fold to the intersection with the angular folds, are the same.

4. A stent according to claim 1, wherein the angular folds are folds of a second type inverse to said first type and the portions of the central longitudinal fold extending from a respective one of the transverse edge folds to a respective intersection with the angular folds are folds of said first type.

5. A stent according to claim 1, wherein the angular folds all intersect the central longitudinal fold at the same position.

6. A stent according to claim 1, wherein said pairs of angular folds intersect the central longitudinal fold at separated positions between which the central longitudinal fold is a fold of said second type.

7. A stent according to claim 1, wherein the angle between a transverse edge fold and an angular fold is 45°.

8. A stent according to claim 1, wherein the angle between a transverse edge fold and an angular fold is less than 45°.

9. A stent according to claim 1, wherein the angle between a transverse edge fold and an angular fold is greater than 45° and less than or equal to 60°.

10. A stent according to claim 1, wherein the unit cell further comprises a ring of folds of said second type each parallel to an adjacent edge fold, the pattern of folds inside the ring of folds of said second type reversing from folds of said first type to folds of said second type and vice versa.

11. A stent according to claim 1, wherein the unit cell is symmetrical about the central longitudinal fold.

12. A stent according to claim 1, wherein the unit cell is symmetrical about an imaginary line extending around the tube.

13. A stent according to claim 1, wherein the folds of said first type are hill folds and the folds of said second type are valley folds.

14. A stent according to claim 1, wherein the pattern of folds comprises a single unit cell repeated over the entire sheet.

15. A stent according to claim 1, wherein the pattern of folds comprises a plurality of rows of unit cells extending around the tube.

16. A stent according to claim 15, wherein at least two of the rows comprise a respective, different unit cell repeated around the tube.

17. A stent according to claim 1, wherein the pattern of folds comprises a plurality of rows of unit cells extending around the tube and the unit cells of adjacent rows are offset with the longitudinal edge folds of each row meeting the central longitudinal folds of the adjacent rows.

18. A stent according to claim 17, wherein the longitudinal edge folds of alternate rows and the central longitudinal folds which meet form an uninterrupted fold line progressing helically around the tube.

19. A stent according to claim 1, wherein the pattern of folds comprises at least one row of unit cells progressing helically around the tube.

20. A stent according to claim 19, wherein the pattern of folds comprises two rows of unit cells each two rows progressing helically around the tube.

21. A stent according to claim 1, wherein the sheet has apertures at at least some of the nodes where folds intersect.

22. A stent according to claim 1, wherein the sheet has edges joined along the length of the tube.

23. A stent according to claim 1, wherein the sheet is continuous around the tube.

24. A stent according to claim 1, wherein the outer surface of the sheet on the outer side of the tube has a higher degree of friction than the inner surface of the sheet on the inner side of the tube.

25. A stent according to claim 24, wherein the outer surface of the sheet on the outer side of the tube is roughened.

26. A stent according to claim 24, wherein the outer surface of the sheet on the outer side of the tube has a sufficient degree of friction to provide anchorage at an anatomical site.

27. A planar sheet of biocompatible material having opposed edges and a pattern of fold lines arranged to allow the sheet to be folded into a tube with the opposed edges adjacent one another to form a stent which is collapsible for deployment, the pattern of folds comprising a unit cell repeated over at least a portion of the sheet, the unit cell comprising:

an outer circumferential edge of folds of a first type comprising a pair of longitudinal edge folds extending along the tube and transverse edge folds extending around the tube;

a central longitudinal fold extending along the tube between the transverse edge folds; and angular folds extending from each intersection of a longitudinal edge fold with a transverse edge fold to the central longitudinal fold.

28. A stent comprising a biocompatible sheet arranged as a tube folded with a pattern of folds allowing the stent to be collapsed for deployment, wherein the tube is conical along at least a portion thereof.

29. A stent comprising a biocompatible sheet arranged as a tube folded with a pattern of folds allowing the stent to be collapsed for deployment, wherein the outer surface of the sheet on the outer side of the tube has a higher degree of friction than the inner surface of the sheet on the inner side of the tube.

30. A stent according to claim 29, wherein the outer surface of the sheet on the outer side of the tube is roughened.

31. A stent according to claim 29, wherein the outer surface of the sheet on the outer side of the tube has a sufficient degree of friction to provide anchorage at an anatomical site.

* * * * *